(12) United States Patent
Vijayaraghavan et al.

(10) Patent No.: US 12,082,977 B2
(45) Date of Patent: Sep. 10, 2024

(54) THERMALLY CONDUCTIVE SHOCK ABSORBERS FOR MEDICAL IMAGING PROBES

(71) Applicant: GE Precision Healthcare LLC, Wauwatosa, WI (US)

(72) Inventors: Sanjay Vijayaraghavan, Bangalore (IN); Steffen Fleischer, Lohnsburg (AT); Warren Lee, Niskayuna, NY (US); Ashif Iqbal, Bangalore (IN)

(73) Assignee: GE Precision Healthcare LLC, Waukesha, WI (US)

( * ) Notice: Subject to any disclaimer, the term of this patent is extended or adjusted under 35 U.S.C. 154(b) by 0 days.

(21) Appl. No.: 17/583,439

(22) Filed: Jan. 25, 2022

(65) Prior Publication Data

US 2023/0233191 A1    Jul. 27, 2023

(51) Int. Cl.
   *A61B 8/00*   (2006.01)
(52) U.S. Cl.
   CPC .......... *A61B 8/546* (2013.01); *A61B 8/4444* (2013.01); *A61B 8/4494* (2013.01)
(58) Field of Classification Search
   CPC ... A61B 8/4444; A61B 8/546; G01S 7/52079; G01S 7/5208; F16F 2230/10
   See application file for complete search history.

(56) References Cited

U.S. PATENT DOCUMENTS

| 2006/0100513 | A1* | 5/2006 | Hashimoto | .......... G10K 11/004 600/437 |
| 2006/0261707 | A1* | 11/2006 | Wildes | ................ A61B 8/546 310/346 |
| 2013/0172751 | A1* | 7/2013 | Heinrich | .............. A61B 8/4483 600/447 |
| 2020/0260614 | A1* | 8/2020 | Kim | .................. H05K 7/20481 |
| 2021/0112685 | A1* | 4/2021 | Magi | ...................... G06F 1/203 |
| 2021/0275151 | A1* | 9/2021 | Clark | .................... B06B 1/0685 |
| 2022/0117580 | A1* | 4/2022 | Bryzek | ................ A61B 8/4488 |

* cited by examiner

*Primary Examiner* — Colin T. Sakamoto
*Assistant Examiner* — Tommy T Ly
(74) *Attorney, Agent, or Firm* — McAndrews, Held & Malloy, Ltd.; Daniel Bissing; David Bates

(57) ABSTRACT

Systems and methods are provided for thermally conductive shock absorbers for medical imaging probes. An example medical imaging probe may have, at least, a transducer disposed underneath a contact surface of the medical imaging probe, with the transducer configured to transmit and receive signals based on a medical imaging technique; a support structure disposed underneath the transducer; and a thermally conductive shock absorber (TCSA) layer disposed between the transducer and the support structure, with the thermally conductive shock absorber (TCSA) layer is configured to facilitate both of thermal transfer in a direction from the contact surface into the support structure, and absorbing at least a portion of impact force applied to at least the contact surface. The support structure may include a heat sink.

20 Claims, 13 Drawing Sheets

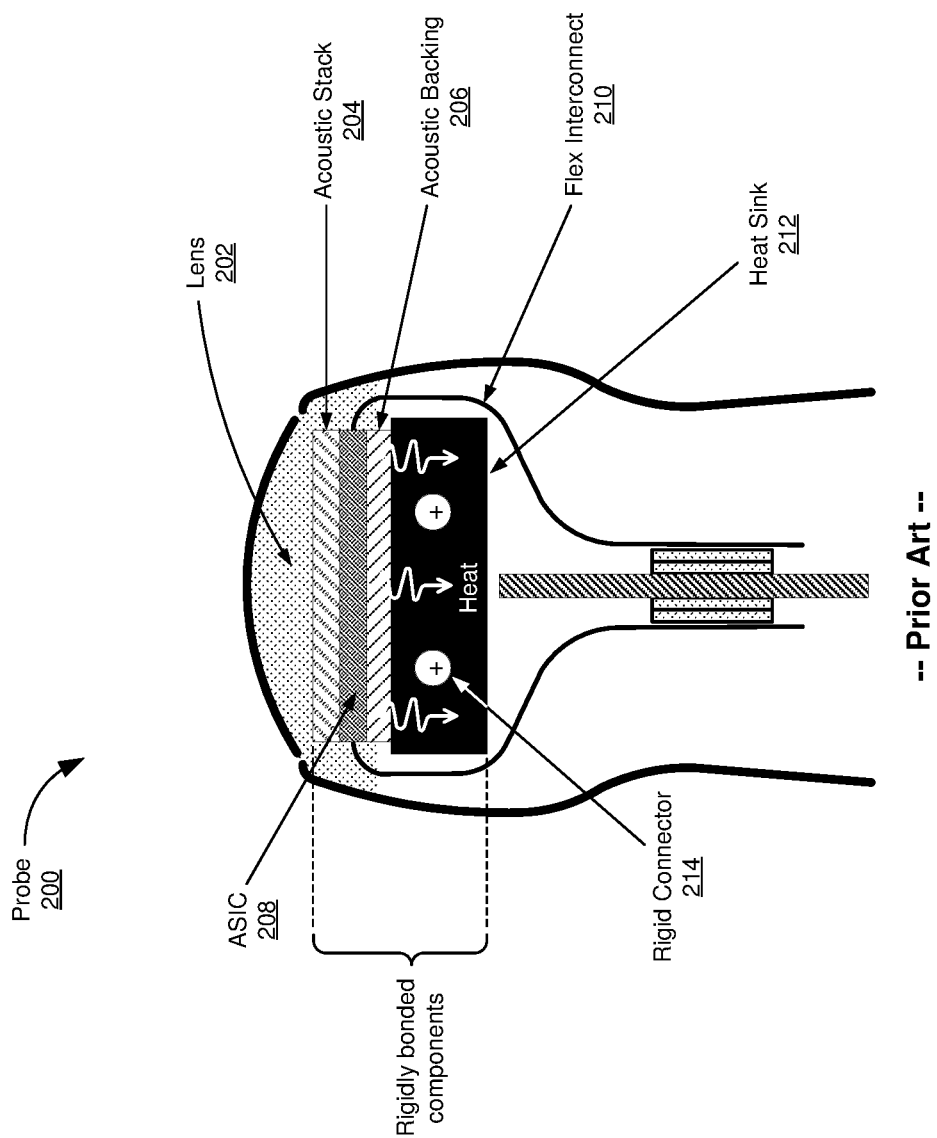
FIG. 2 -- Prior Art --

THERMALLY CONDUCTIVE SHOCK ABSORBERS FOR MEDICAL IMAGING PROBES

FIELD

Aspects of the present disclosure relate to medical imaging solutions. More specifically, certain embodiments relate to methods and systems for thermally conductive shock absorbers for medical imaging probes.

BACKGROUND

Various medical imaging techniques may be used, such as in imaging organs and soft tissues in a human body. Examples of medical imaging techniques include ultrasound imaging, computed tomography (CT) scans, magnetic resonance imaging (MRI), etc. The manner by which images are generated during medical imaging depends on the particular technique.

For example, ultrasound imaging uses real time, non-invasive high frequency sound waves to produce ultrasound images, typically of organs, tissues, objects (e.g., fetus) inside the human body. Images produced or generated during medical imaging may be two-dimensional (2D), three-dimensional (3D), and/or four-dimensional (4D) images (essentially real-time/continuous 3D images). During medical imaging, imaging datasets (including, e.g., volumetric imaging datasets during 3D/4D imaging) are acquired and used in generating and rendering corresponding images (e.g., via a display) in real-time.

In some instances, operation of certain components of medical imaging systems, such as the medical imaging probes, may pose certain challenges, particularly in conjunction with conditions that may cause damage to these components, and conventional and traditional approaches may not sufficiently address or overcome these challenges.

Further limitations and disadvantages of conventional and traditional approaches will become apparent to one of skill in the art, through comparison of such systems with some aspects of the present disclosure, as set forth in the remainder of the present application with reference to the drawings.

BRIEF SUMMARY

System and methods are provided for thermally conductive shock absorbers for medical imaging probes, substantially as shown in and/or described in connection with at least one of the figures, as set forth more completely in the claims.

These and other advantages, aspects and novel features of the present disclosure, as well as details of one or more illustrated example embodiments thereof, will be more fully understood from the following description and drawings.

BRIEF DESCRIPTION OF THE DRAWINGS

FIG. 2 is a block diagram illustrating an example medical imaging probe without thermally conductive shock absorber (TCSA) layer.

DETAILED DESCRIPTION

Figure 1:
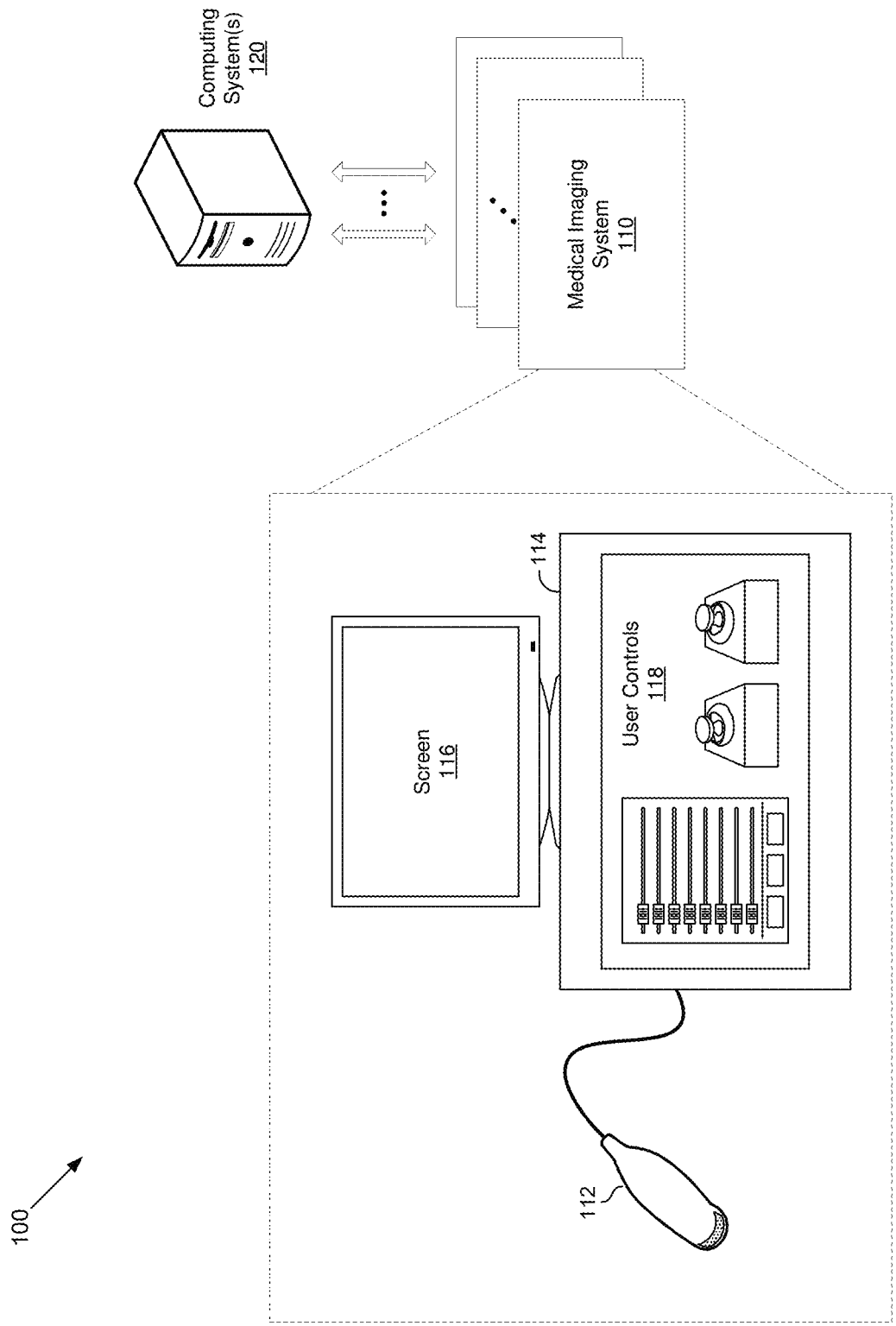
FIG. 1 is a block diagram illustrating an example medical imaging arrangement.

Certain implementations in accordance with the present disclosure may be directed to thermally conductive shock absorbers for medical imaging probes. In particular, the following detailed description of certain embodiments will be better understood when read in conjunction with the appended drawings. To the extent that the figures illustrate diagrams of the functional blocks of various embodiments, the functional blocks are not necessarily indicative of the division between hardware circuitry. Thus, for example, one or more of the functional blocks (e.g., processors or memories) may be implemented in a single piece of hardware (e.g., a general purpose signal processor or a block of random access memory, hard disk, or the like) or multiple pieces of hardware. Similarly, the programs may be stand-alone programs, may be incorporated as subroutines in an operating system, may be functions in an installed software package, and the like. It should be understood that the various embodiments are not limited to the arrangements and instrumentality shown in the drawings. It should also be understood that the embodiments may be combined, or that other embodiments may be utilized and that structural, logical and electrical changes may be made without departing from the scope of the various embodiments. The following detailed description is, therefore, not to be taken in a limiting sense, and the scope of the present disclosure is defined by the appended claims and their equivalents.

As used herein, an element or step recited in the singular and preceded with the word "a" or "an" should be understood as not excluding plural of said elements or steps, unless such exclusion is explicitly stated. Furthermore, references to "an exemplary embodiment," "various embodiments," "certain embodiments," "a representative embodiment," and the like are not intended to be interpreted as excluding the existence of additional embodiments that also incorporate the recited features. Moreover, unless explicitly stated to the contrary, embodiments "comprising," "including," or "having" an element or a plurality of elements having a particular property may include additional elements not having that property.

Also as used herein, the term "image" broadly refers to both viewable images and data representing a viewable image. However, many embodiments generate (or are configured to generate) at least one viewable image. In addition, as used herein, the phrase "image" as used in the context of ultrasound imaging is used to refer to an ultrasound mode such as B-mode (2D mode), M-mode, three-dimensional (3D) mode, CF-mode, PW Doppler, CW Doppler, MGD, and/or sub-modes of B-mode and/or CF such as Shear Wave Elasticity Imaging (SWEI), TVI, Angio, B-flow, BMI, BMI_Angio, and in some cases also MM, CM, TVD where the "image" and/or "plane" includes a single beam or multiple beams.

In addition, as used herein, the phrase "pixel" also includes embodiments where the data is represented by a "voxel." Thus, both the terms "pixel" and "voxel" may be used interchangeably throughout this document.

Furthermore, the term processor or processing unit, as used herein, refers to any type of processing unit that can carry out the required calculations needed for the various embodiments, such as single or multi-core: CPU, Accelerated Processing Unit (APU), Graphics Board, DSP, FPGA, ASIC, or a combination thereof.

It should be noted that various embodiments described herein that generate or form images may include processing for forming images that in some embodiments includes beamforming and in other embodiments does not include beamforming. For example, an image can be formed without beamforming, such as by multiplying the matrix of demodulated data by a matrix of coefficients so that the product is the image, and wherein the process does not form any "beams". In addition, forming of images may be performed using channel combinations that may originate from more than one transmit event (e.g., synthetic aperture techniques).

In various embodiments, processing to form images is performed in software, firmware, hardware, or a combination thereof. The processing may include use of beamforming.

FIG. 1 is a block diagram illustrating an example medical imaging arrangement. Shown in FIG. 1 is an example medical imaging arrangement 100 that comprises one or more medical imaging systems 110 and one or more computing systems 120. The medical imaging arrangement 100 (including various elements thereof) may be configured to support medical imaging and solutions associated therewith.

The medical imaging system 110 comprise suitable hardware, software, or a combination thereof, for supporting medical imaging—that is enabling obtaining data used in generating and/or rendering images during medical imaging exams. Examples of medical imaging include ultrasound imaging, computed tomography (CT) scans, magnetic resonance imaging (MRI), etc. This may entail capturing of particular type of data, in particular manner, which may in turn be used in generating data for the images. For example, the medical imaging system 110 may be an ultrasound imaging system, configured for generating and/or rendering ultrasound images.

As shown in FIG. 1, the medical imaging system 110 may comprise a scanner device 112, which may be portable and movable, and a display/control unit 114. The scanner device 112 may be configured for generating and/or capturing particular type of imaging signals (and/or data corresponding thereto), such as by being moved over a patient's body (or part thereof), and may comprise suitable circuitry for performing and/or supporting such functions. The scanner device 112 may be an ultrasound probe, MRI scanner, CT scanner, or any suitable imaging device. For example, where the medical imaging system 110 is an ultrasound system, the scanner device 112 may emit ultrasound signals and capture echo ultrasound images.

The display/control unit 114 may be configured for displaying images (e.g., via a screen 116). In some instances, the display/control unit 114 may further be configured for generating the displayed images, at least partly. Further, the display/control unit 114 may also support user input/output. For example, the display/control unit 114 may provide (e.g., via the screen 116), in addition to the images, user feedback (e.g., information relating to the system, functions thereof, settings thereof, etc.). The display/control unit 114 may also support user input (e.g., via user controls 118), such as to allow controlling of the medical imaging. The user input may be directed to controlling display of images, selecting settings, specifying user preferences, requesting feedback, etc.

In some implementations, the medical imaging arrangement 100 may also incorporate additional and dedicated computing resources, such as the one or more computing systems 120. In this regard, each computing system 120 may comprise suitable circuitry, interfaces, logic, and/or code for processing, storing, and/or communication data. The computing system 120 may be dedicated equipment configured particularly for use in conjunction with medical imaging, or it may be a general purpose computing system (e.g., personal computer, server, etc.) set up and/or configured to perform the operations described hereinafter with respect to the computing system 120. The computing system 120 may be configured to support operations of the medical imaging systems 110, as described below. In this regard, various functions and/or operations may be offloaded from the imaging systems. This may be done to streamline and/or centralize certain aspects of the processing, to reduce cost—e.g., by obviating the need to increase processing resources in the imaging systems.

The computing systems 120 may be set up and/or arranged for use in different ways. For example, in some implementations a single computing system 120 may be used; in other implementations multiple computing systems 120, either configured to work together (e.g., based on distributed-processing configuration), or separately, with each computing system 120 being configured to handle particular aspects and/or functions, and/or to process data only for particular medical imaging systems 110. Further, in some implementations, the computing systems 120 may be local (e.g., co-located with one or more medical imaging systems 110, such within the same facility and/or same local network); in other implementations, the computing systems 120 may be remote and thus can only be accessed via remote connections (e.g., via the Internet or other available remote access techniques). In a particular implementation, the computing systems 120 may be configured in cloud-based manner, and may be accessed and/or used in substantially similar way that other cloud-based systems are accessed and used.

Once data is generated and/or configured in the computing system 120, the data may be copied and/or loaded into the medical imaging systems 110. This may be done in different ways. For example, the data may be loaded via directed connections or links between the medical imaging systems 110 and the computing system 120. In this regard, communications between the different elements in the medical imaging arrangement 100 may be done using available wired and/or wireless connections, and/or in accordance any suitable communication (and/or networking) standards or protocols. Alternatively, or additionally, the data may be loaded into the medical imaging systems 110 indirectly. For example, the data may be stored into suitable machine readable media (e.g., flash card, etc.), which are then used to load the data into the medical imaging systems 110 (on-site, such as by users of the systems (e.g., imaging clinicians) or authorized personnel), or the data may be downloaded into local communication-capable electronic devices (e.g., laptops, etc.), which are then used on-site (e.g., by users of the systems or authorized personnel) to upload the data into the medical imaging systems 110, via direct connections (e.g., USB connector, etc.).

In operation, the medical imaging system 110 may be used in generating and presenting (e.g., rendering or displaying) images during medical exams, and/or in supporting user input/output in conjunction therewith. The images may be 2D, 3D, and/or 4D images. The particular operations or functions performed in the medical imaging system 110 to facilitate the generating and/or presenting of images depends on the type of system—that is, the manner by which the data corresponding to the images is obtained and/or generated. For example, in ultrasound imaging, the data is based on emitted and echo ultrasound signals. In computed tomography (CT) scans based imaging, the data is based on emitted and captured x-rays signals.

In various implementations in accordance with the present disclosure, medical imaging systems and/or architectures (e.g., the medical imaging system 110 and/or the medical imaging arrangement 100 as a whole) may be configured to support implementing and utilizing medical imaging probes with thermally conductive shock absorber(s). In this regard, medical imaging probes (e.g., ultrasound probes) may contain fragile components. These components may reside near the contact surface of the probe and may be prone to damage or breakage, particularly under certain conditions such as during drop and impact events. These components may also dissipate heat, which may result in thermally-limited performance. Therefore, there is a need for solutions that may allow for increasing robustness of the probes, while maintaining (or even improving) thermal performance of the probes.

Solutions in accordance with the present disclosure may addresses such issues, and particularly do so in low-cost manner. This may be done by utilizing low-cost, easy-to-implement thermally conductive shock absorber (TCSA) material or components, which may be incorporated into the probes to provide compliance for drop robustness while maintaining a thermal pathway for the transfer of heat (e.g., from the transducer assembly to the thermal management components of the probes). Example implementations and additional details related thereto are described in more detail below, with respect to FIGS. 2-10.

FIG. 2 is a block diagram illustrating an example medical imaging probe without thermally conductive shock absorber (TCSA) layer. Shown in FIG. 2 is a medical imaging probe (or portion thereof) 200 implemented in accordance with conventional solutions—that is, the probe 200 does not incorporate thermally conductive shock absorber (TCSA) related components.

As illustrated in FIG. 2, the probe 200 is configured for ultrasound imaging operations. In this regard, the probe 200 comprises a transducer assembly that is configured to transmit and receive acoustic (e.g., ultrasonic) signals for use in conjunction with ultrasound imaging. In particular, the transducer assembly of the probe 200 may comprise an acoustic stack 204, processing circuitry (e.g., application-specific integrated circuit (ASIC)) 208, and an acoustic stack 206. The processing circuity (e.g., ASIC 208) may be connected using flex interconnect(s) 210, which may be used to provide power and/or control signals to the processing signals (e.g., from the ultrasound system) and/or to communicate received (echo) signals or data related thereto as obtained in the processing circuitry. The transducer assembly may be disposed within a lens (section) 202, which may be filled with compliant lens material. Further the transducer assembly may be disposed on top of, and be integrated into a supporting mechanical assembly, which may comprise a heat sink 212.

In many instances, transducer assembly in medical imaging probe such as the probe 200 may be heat-dissipating. In this regard, the transducer assembly may be heat-dissipating as at least some of the components of the transducer assembly (e.g., the acoustic stack 204, the ASIC 208) may generate heat. For thermal management, the transducer assembly (including the ASIC) are tightly integrated and rigidly connected to other parts of the probe assembly, which may include thermal management components such as a heat sink 212 and a heat spreader (not shown), through which generated heat may pass and be dissipated. These components may in turn be attached to a rigid internal support and probe housing (e.g., using rigid connector(s) 214, which provide rigid connection to heat spreader and/or internal support, housing. When the probe is dropped and the transducer assembly end is impacted, the impact force may be transmitted directly to the fragile components of the probe, such as the acoustic stack and the ASIC, which may lead to irreparable damage to the probe since there is no compliance or shock absorbing component within the internal assembly.

Solutions in accordance with the present disclosure address some of these issues, particularly by incorporating new features that may further assist (or at least not hinder) thermal management function while concurrently providing impact absorbing improvement in the probe. Example implementations based on such solutions are described in more detail below. Nonetheless, while these example implementations are described with respect to ultrasound probe, the disclosure is not so limited, and solutions in accordance with the present disclosure may be used, in substantially similar manner, into other types of medical imaging probes.

Figure 3A:
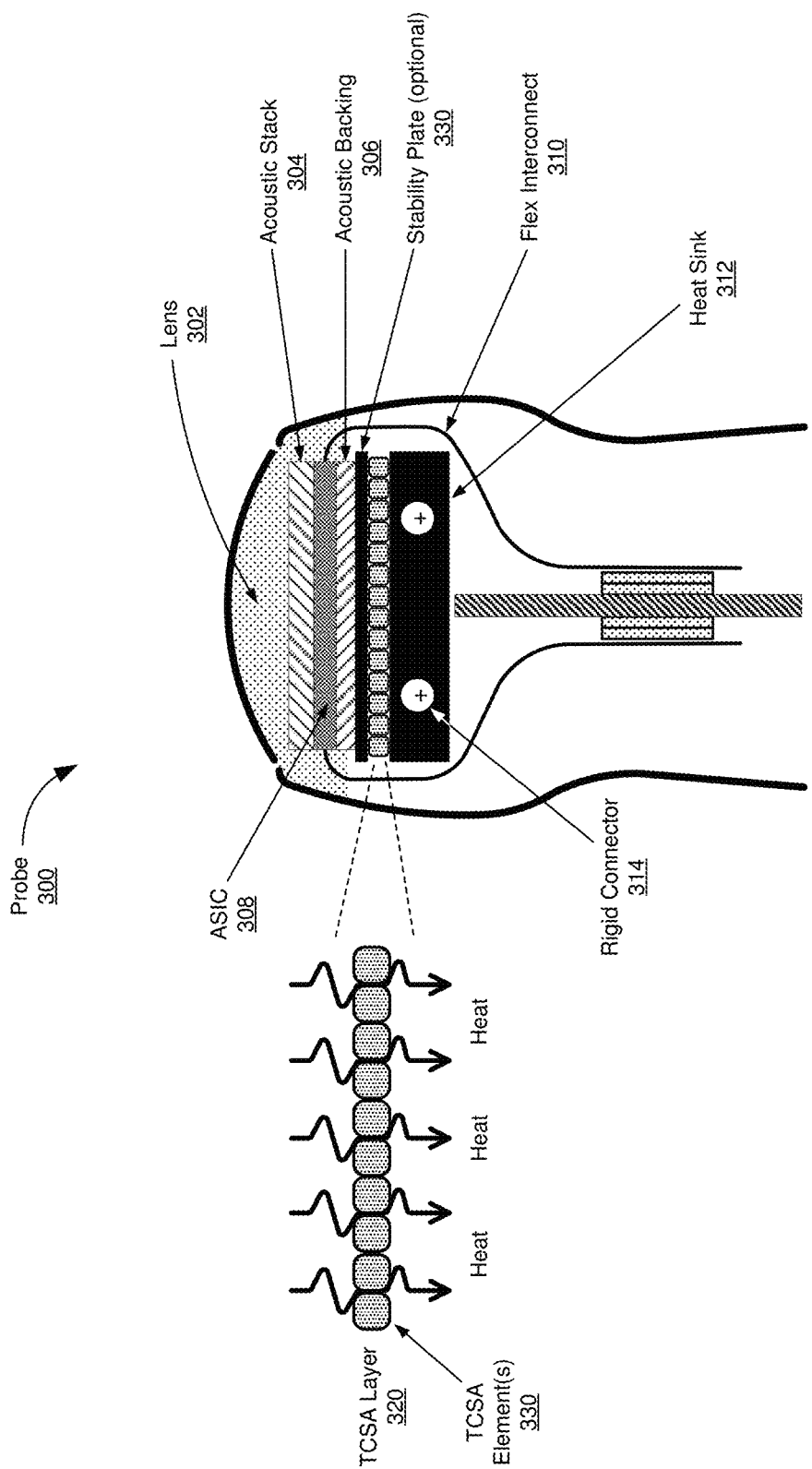
FIGS. 3A-3C are block diagrams illustrating an example medical imaging probe with thermally conductive shock absorber (TCSA) layer.
Figure 3B:
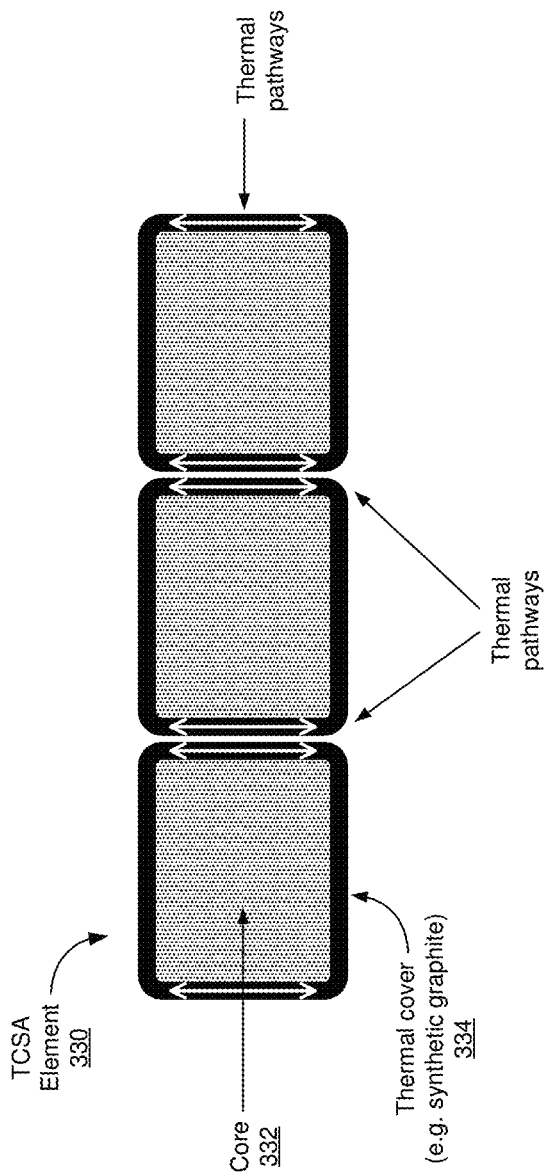
Figure 3C:
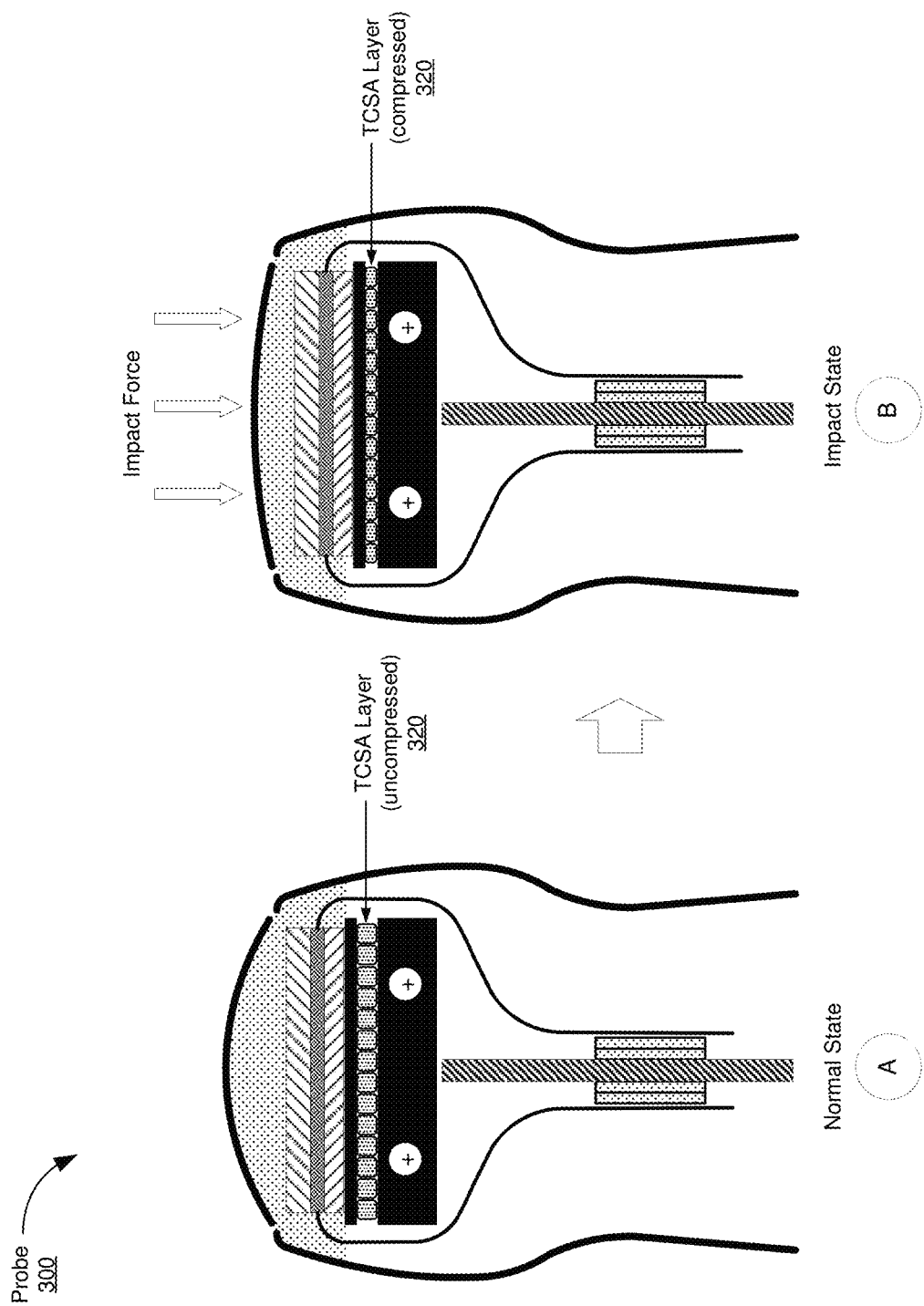

FIGS. 3A-3C are block diagrams illustrating an example medical imaging probe with thermally conductive shock absorber (TCSA) layer. Shown in FIGS. 3A-3C is a medical imaging probe (or portion thereof) 300, which is implemented in accordance with the present disclosure—that is, with thermally conductive shock absorber (TCSA) related components and features.

The probe 300 may be similar to the probe 200—that is, being configured for ultrasound imaging, and comprising similar components for facilitating use in similar manner with respect to supporting ultrasound imaging operation. Thus, the probe 300 may similarly comprise a transducer assembly, which may comprise an acoustic stack 304, processing circuitry (e.g., application-specific integrated circuit (ASIC)) 308, and an acoustic stack 306, flex interconnect(s) 310 for connecting to and interacting with the processing circuitry 308, a supporting mechanical assembly that comprises a heat sink 312 that is attached to a rigid internal support and probe housing using rigid connector(s) 314. In this regard, these components may be similar to the similarly-named ones in the probe 200.

However, the probe 300 incorporates thermally conductive shock absorber (TCSA) related components and features. In this regard, as shown in the example implementation illustrated in FIG. 3A, a thermally conductive shock absorber (TCSA) layer 320 is inserted in probe 300, specifically between the transducer assembly and the supporting mechanical assembly below it within the probe. In this regard, as illustrated in FIGS. 3A-3C, the supporting mechanical assembly comprises the heat sink 312. However, the disclosure is not limited to embodiments that include heat sinks, and as such in some embodiments the TCSA layer may reside between the transducer and whatever supporting structures are underneath, whether they are a heat sink, heat spreader, or other internal probe components. The thermally conductive shock absorber (TCSA) layer 320 may be configured to allow transfer (thus dissipation) of heat generated in the transducer assembly into the thermal management components (e.g., the heat sink 312) while also helping with handling impact forces that may be applied to the probe 300. Further, a stability plate 330 optionally may be used in some implementation, for providing mechanical stability to the TCSA layer 320.

Various designs and implementations may be used for the TCSA layer. For example, in some implementations, the TCSA layer 320 may comprise TCSA elements arranged in optimal manner. For example, the TCSA layer 320 may comprise one or more TCSA elements 330. As shown in FIG. 3B, each of the TCSA elements 330 may be comprise an interior core 332 comprised of flexible material (e.g., foam and similar material) and a thermal cover 334 comprised of highly thermally conductive material (e.g., synthetic graphite). The TCSA elements 330 may be implemented using commercially available material.

The design of the TSCA elements 330, as shown in FIG. 3B, provides a highly thermally conductive cover wrapped around a foam core in order to provide a compressible (e.g., foam based) thermal core. The thermally conductive cover provides a low thermal resistance pathway along the outside while the core provides a soft, compressible overall feel. Unlike conventional thermal pads that have a "putty-like" consistency, designs similar to that of the TCSA elements 330 as shown in FIG. 3B may have desirable property of repeatable compression and rebound, while also being extremely lightweight and having optimal thermal performance, and may also be used in various way—e.g., multiple pieces that may be laid down side by side to reduce thermal resistance.

As illustrated in FIG. 3C, due to the compliant nature of the TCSA layer 320 and lens material surrounding the transducer assembly, the transducer assembly in effect mechanically "floats" somewhat independently from the rest of the rigidly assembled probe. In the normal state (reference 'A'), the TCSA layer 320 allows heat to pass from the transducer assembly and ASIC to the heat sink and onto the rest of the probe assembly. During an impact state (reference 'B'), where an impact force may be applied to the transducer assembly end of the probe, the impact force is transmitted to the TCSA layer 320 and the energy is absorbed by the temporary compression of the TCSA layer 320 material, rather than being absorbed by the transducer assembly itself, thus decreasing the likelihood of damage (e.g., a catastrophic brittle failure to acoustic stack 304 and/or the ASIC 308). After the impact, the TCSA layer 320 rebounds to its original shape.

Figure 4:
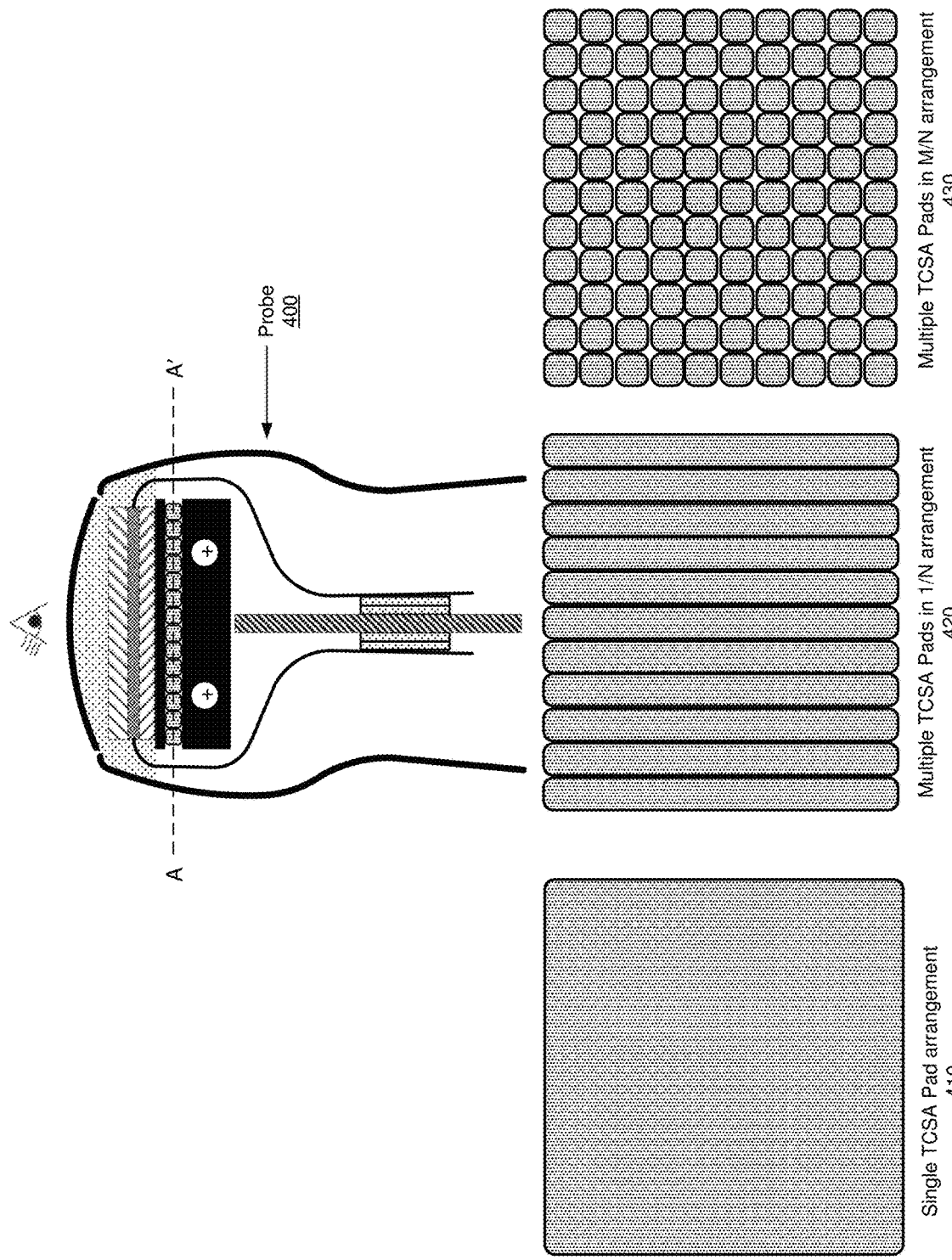
FIG. 4 is a block diagram illustrating various example arrangements of thermally conductive shock absorber (TCSA) in a medical imaging probe.

FIG. 4 is a block diagram illustrating various example arrangements of thermally conductive shock absorber (TCSA) in a medical imaging probe. Shown in FIG. 4 is a probe 400 which may be similar to the probe 300 of FIGS. 3A-3C.

The probe 400 may similarly incorporate a thermally conductive shock absorber (TCSA) layer. In this regard, illustrated in FIG. 4 is various example arrangements (as would appear from overhead perspective of the probe 400— that is, from top view at cross section A-A') that may be used for the TCSA layer. In this regard, to reduce the thermal resistance of the TCSA layer, the different arrangements may provide multiple (and different) thermal pathways, such as by utilizing a 1D or 2D arrays of TCSA elements. For example, Single TCSA Pad arrangement 410 may be used such as in probe with minimal/little heat. Alternatively, in probes with more heat, multiple TCSA pads in 1/N arrangement 420 and/or multiple TCSA pads in M/N arrangement 430.

Figure 5:
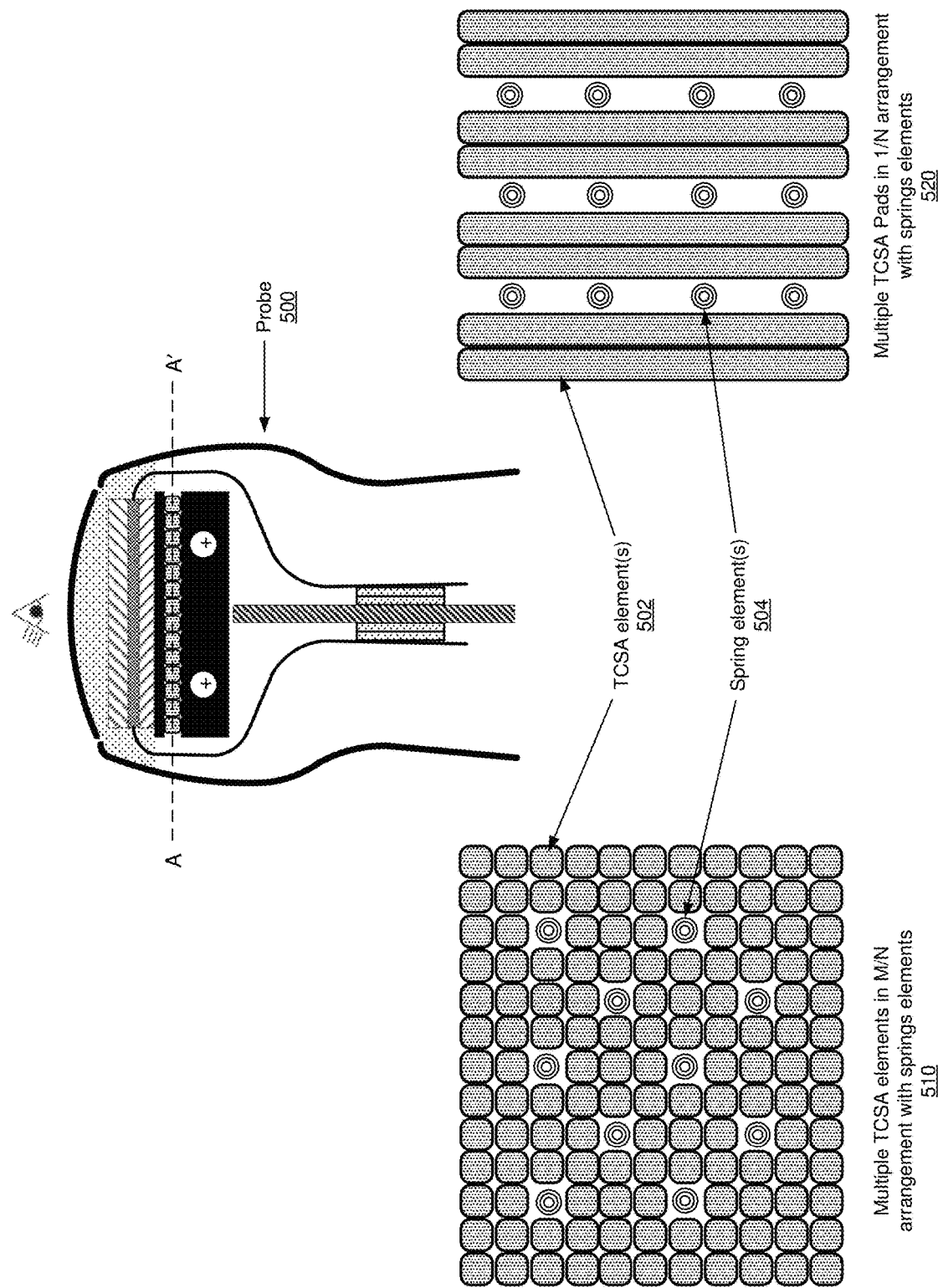
FIG. 5 is a block diagram illustrating various example arrangements of thermally conductive shock absorber (TCSA) with spring elements in a medical imaging probe.

FIG. 5 is a block diagram illustrating various example arrangements of thermally conductive shock absorber (TCSA) with spring elements in a medical imaging probe. Shown in FIG. 5 is a probe 500 which may be similar to the probe 300 of FIGS. 3A-3C.

The probe 500 may similarly incorporate a thermally conductive shock absorber (TCSA) layer. In this regard, illustrated in FIG. 5 is various example arrangements (as would appear from overhead perspective of the probe 500— that is, from top view at cross section A-A') that may be used in enhancing mechanical stiffness the TCSA layer. In this regard, the mechanical stiffness of the TCSA layer may be tuned by, for example, replacing a portion of the TCSA layer (or TCSA elements 502 thereof) with one or more stiffness elements (e.g., "spring" elements) 504, which may control the overall stiffness of the TCSA layer. The spring elements 504 may be of any suitable design. For example, the spring elements 504 may be coiled springs or simply alternative materials with stiffness different than the TCSA layer.

Figure 6:
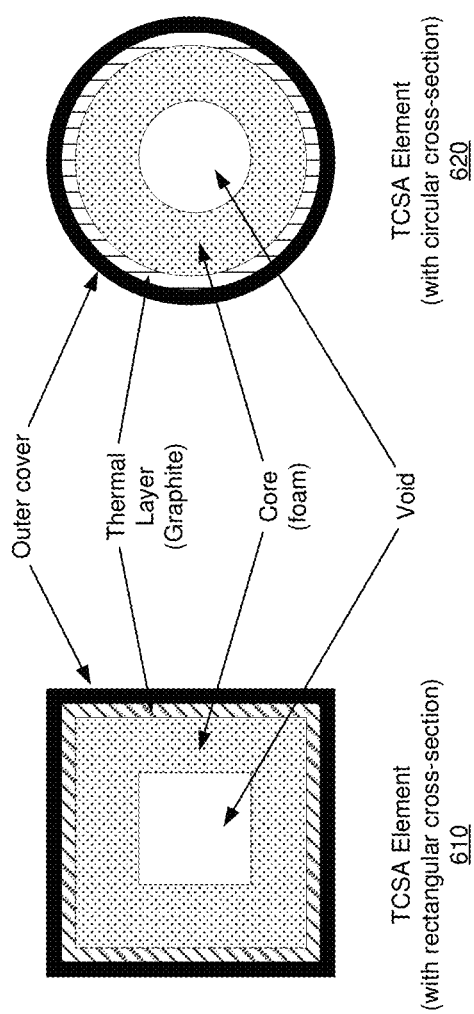
FIG. 6 is a block diagram illustrating various example thermally conductive shock absorber (TCSA) elements.

FIG. 6 is a block diagram illustrating various example thermally conductive shock absorber (TCSA) elements. Shown in FIG. 6 are TCSA elements 610 and 620, which may represent alternative example designs for TCSA elements that may be used in TCSA layers utilized in probes implemented in accordance with the present disclosure.

In this regard, the mechanical stiffness of the TCSA layer may be tuned by changing the properties of the individual TCSA elements. The TCSA elements may comprise a core comprise flexible material (e.g., foam core), and a thermal layer (e.g., synthetic graphite), as well as (optionally) additional layers, such as an outer covering layer and interior void(s). In this regard, the composition and physical shape and dimensions of the foam core, graphite layer, and outer covering layers may all be modified to change the mechanical properties of the TCSA to a desired stiffness. Further, additional layers internal to the graphite layer can also be included to increase the stiffness if desired. Alternatively, one or more voids may be included in the core to decrease stiffness. For example, as illustrated in FIG. 6, the TCSA element 610 may have rectangular cross-section, whereas the TCSA element 620 may have circular cross-section. Nonetheless, the disclosure is not limited to the designs illustrated in FIG. 6.

Figure 7:
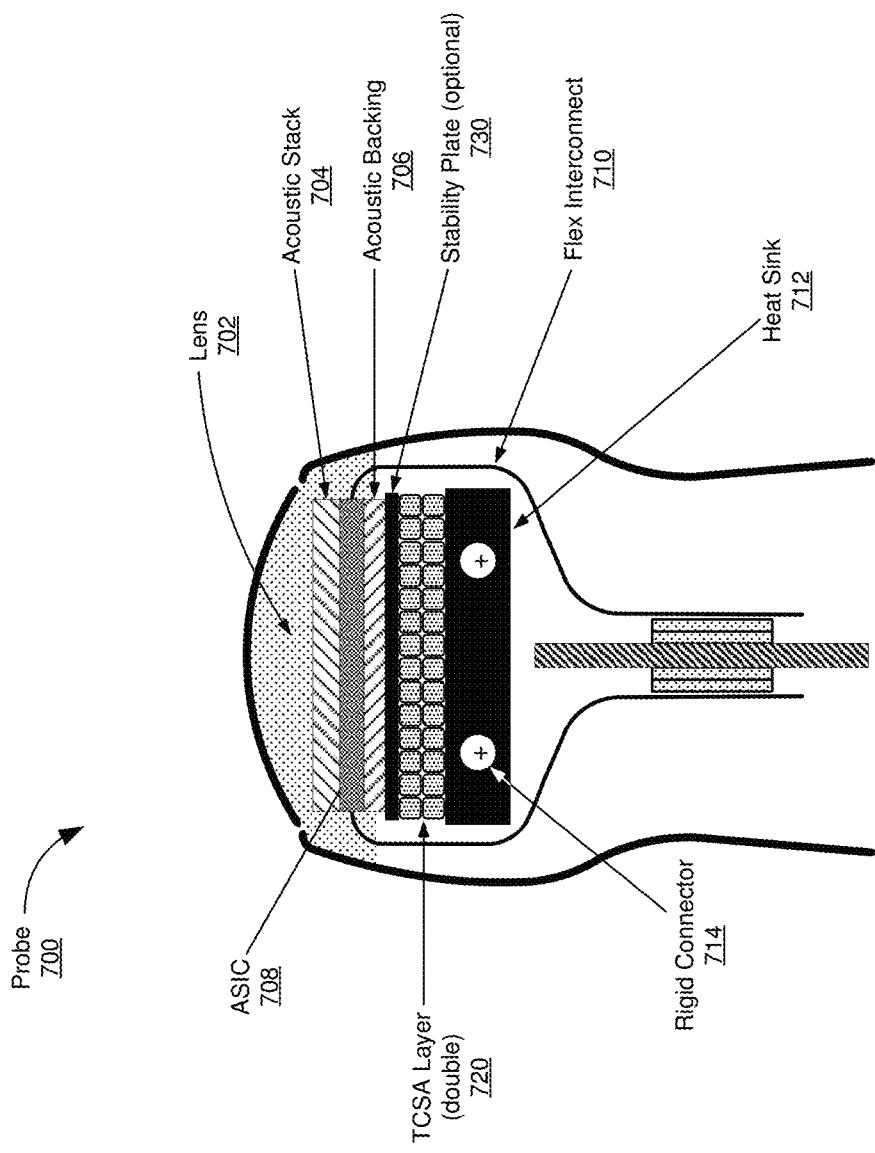
FIG. 7 is a block diagram illustrating an example medical imaging probe with a double thermally conductive shock absorber (TCSA) layer.

FIG. 7 is a block diagram illustrating an example medical imaging probe with a double thermally conductive shock absorber (TCSA) layer. Shown in FIG. 7 is a probe 700 which may be similar to the probe 300 of FIGS. 3A-3C.

The probe 700 may similarly incorporate thermally conductive shock absorber (TCSA) material. Thus, the probe 700 may similarly comprise a transducer assembly, which may comprise an acoustic stack 704, processing circuitry (e.g., application-specific integrated circuit (ASIC)) 708, and an acoustic stack 706, flex interconnect(s) 710 for connecting to and interacting with the processing circuitry 708, a supporting mechanical assembly that comprises a heat sink 712 that is attached to a rigid internal support and probe housing using rigid connector(s) 714, TCSA layer 720, and a stability plate 730. In this regard, these components may be similar to the similarly-named ones in the probe 300.

However, as illustrated in FIG. 7, the TCSA layer 720 used in the probe 700 may be implemented as a double TCSA layer—that is with two levels of TCSA elements. In this regard, the mechanical stiffness of the TCSA material (and thus impact handling characteristics of the probe) may be tuned by adjusting thickness and/or number of TCSA layers used in the probe. Accordingly, by using a double TCSA layer, the mechanical stiffness of the probe 700 may be adjusted compared to the probe 300. The disclosure is not limited to use of double layer, however, and in other implementations various number of levels may be used (e.g., three or more levels).

Figure 8:
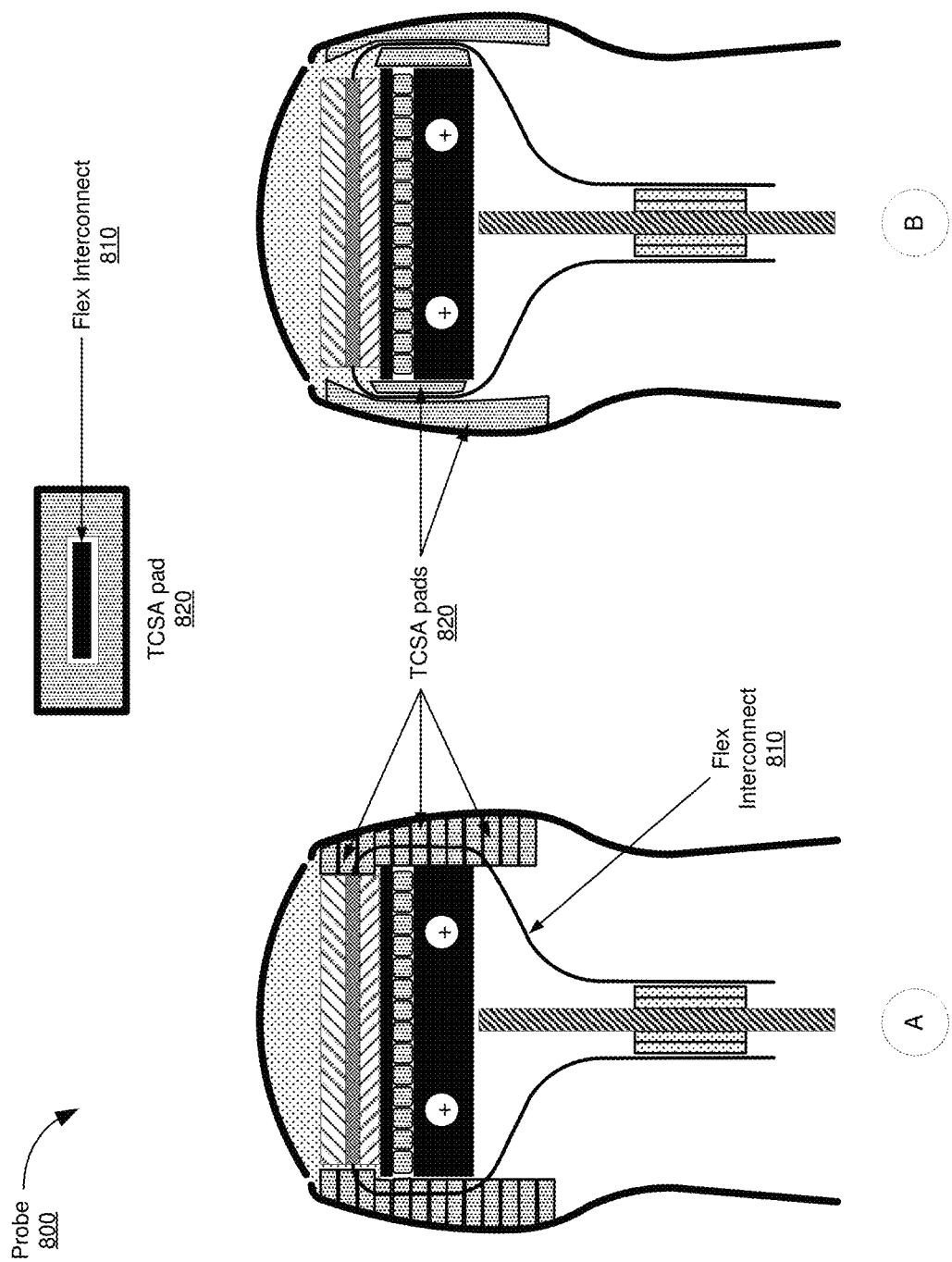
FIG. 8 is a block diagram illustrating an example medical imaging probe with frontal and side thermally conductive shock absorber (TCSA) layers.

FIG. 8 is a block diagram illustrating an example medical imaging probe with frontal and side thermally conductive shock absorber (TCSA) layers. Shown in FIG. 8 is a probe 800 which may be similar to the probe 300 of FIGS. 3A-3C.

The probe 800 may similarly incorporate thermally conductive shock absorber (TCSA) material. However, as illustrated in FIG. 8, in addition to the TCSA layer used between the transducer assembly and the supporting mechanical assembly (including the heat sink), the probe 800 may additionally incorporate TCSA material (e.g., pads) 820 that surround the nose area as shown in FIG. 8.

In this regard, the TCSA pads 820 may be disposed in the side areas surrounding the transducer assembly and the supporting mechanical assembly, to help with impact resistance from side and provide heat flow path to the casing. Thus, the TCSA pads 820 may provide impact protection (with thermal conducting) on the sides in addition to the impact protection (with thermal conducting) provided by the TCSA layer with respect to the frontal/contact surface of the probe. Various designs may be used in incorporating the TCSA pads 820. For example, as shown in A, the TCSA pads 820 may be implemented such that a flex interconnect 810 may be passed through some TCSA pads as needed—that is, with some TCSA pads incorporating internal space for accommodating passing of the flex interconnect 810. Alternatively, as shown in B, the TCSA pads 820 may arranged such that flex interconnect 810 passes between different pads.

Figure 9:
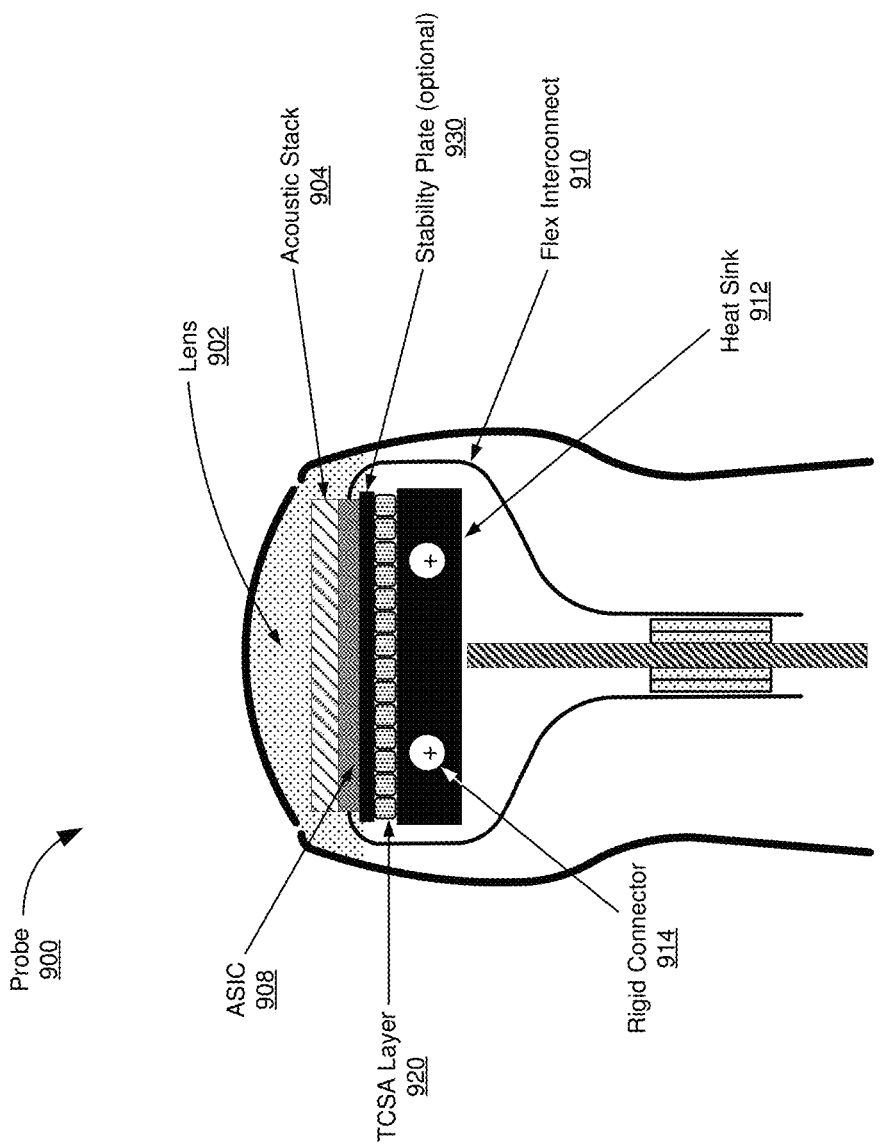
FIG. 9 is a block diagram illustrating an example medical imaging probe with a thermally conductive shock absorber (TCSA) layer and without acoustic backing.

FIG. 9 is a block diagram illustrating an example medical imaging probe with a thermally conductive shock absorber (TCSA) layer and without acoustic backing. Shown in FIG. 8 is a probe 800 which may be similar to the probe 300 of FIGS. 3A-3C.

The probe 900 may similarly incorporate thermally conductive shock absorber (TCSA) material. Thus, the probe 900 may similar comprise a transducer assembly, which may comprise an acoustic stack 904 and processing circuitry (e.g., application-specific integrated circuit (ASIC)) 908, flex interconnect(s) 910 for connecting to and interacting with the processing circuitry 908, a supporting mechanical assembly that comprises a heat sink 912 that is attached to a rigid internal support and probe housing using rigid connector(s) 914, TCSA layer 920, and a stability plate 930. In this regard, these components may be similar to the similarly-named ones in the probe 300.

However, in the probe 900 the TCSA layer may be configured such that it may replace the acoustic backing, thus allowing for its omission from the probe. In this regard, the TCSA layer (or elements thereof) may incorporate foam core which may be comprised primarily of air, and as such there may be a large impedance mismatch with the TCSA layer present. Thus, the TCSA layer may reflect ultrasound energy back, obviating the need for an attenuating acoustic backing. The highly thermally conductive graphite covering on the TCSA layer maintains the thermal pathway between the transducer assembly and the thermal management components in the probe.

Figure 10:
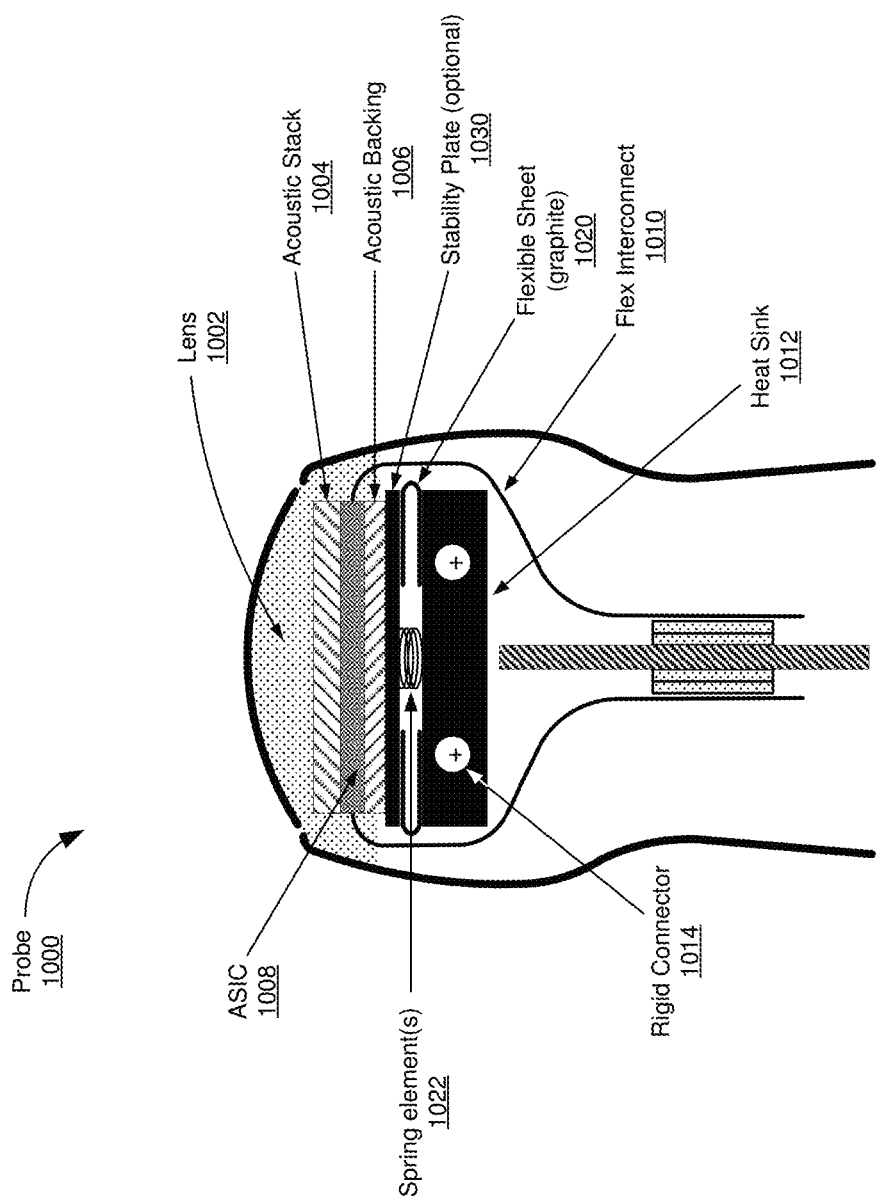
FIG. 10 is a block diagram illustrating an example medical imaging probe with a thermally conductive shock absorber (TCSA) layer using an alternative design based on flexible sheets and spring elements.

FIG. 10 is a block diagram illustrating an example medical imaging probe with a thermally conductive shock absorber (TCSA) layer using an alternative design based on flexible sheets and spring elements. Shown in FIG. 10 is a probe 1000 which may be similar to the probe 300 of FIGS. 3A-3C.

Thus, the probe 1000 may similar comprise a transducer assembly, which may comprise an acoustic stack 1004, processing circuitry (e.g., application-specific integrated circuit (ASIC)) 1008, and an acoustic stack 1006, flex interconnect(s) 1010 for connecting to and interacting with the processing circuitry 1008, a supporting mechanical assembly that comprises a heat sink 1012 that is attached to a rigid internal support and probe housing using rigid connector(s) 1014, and a stability plate 1030. In this regard, these components may be similar to the similarly-named ones in the probe 300. However, unlike the probe 300, the probe 1000 may incorporate thermally conductive shock absorber (TCSA) layer that does not use TCSA material as described above. Rather, the probe 1000 an alternative embodiment employs one or more flexible graphite sheets 1020 that provide the required low thermal resistance pathway between the mechanically floating transducer assembly and the remaining probe assembly (e.g., the supporting mechanical assembly/thermal management components) in the probe. Further, the probe 1000 may incorporate one or more separate spring elements 1022 that may provide mechanical compliance and shock absorbing between the transducer assembly and the remaining probe assembly. For example, the spring elements 1022 may be coiled springs or simply alternative materials with defined stiffness providing compliance and rebound.

Figure 11:
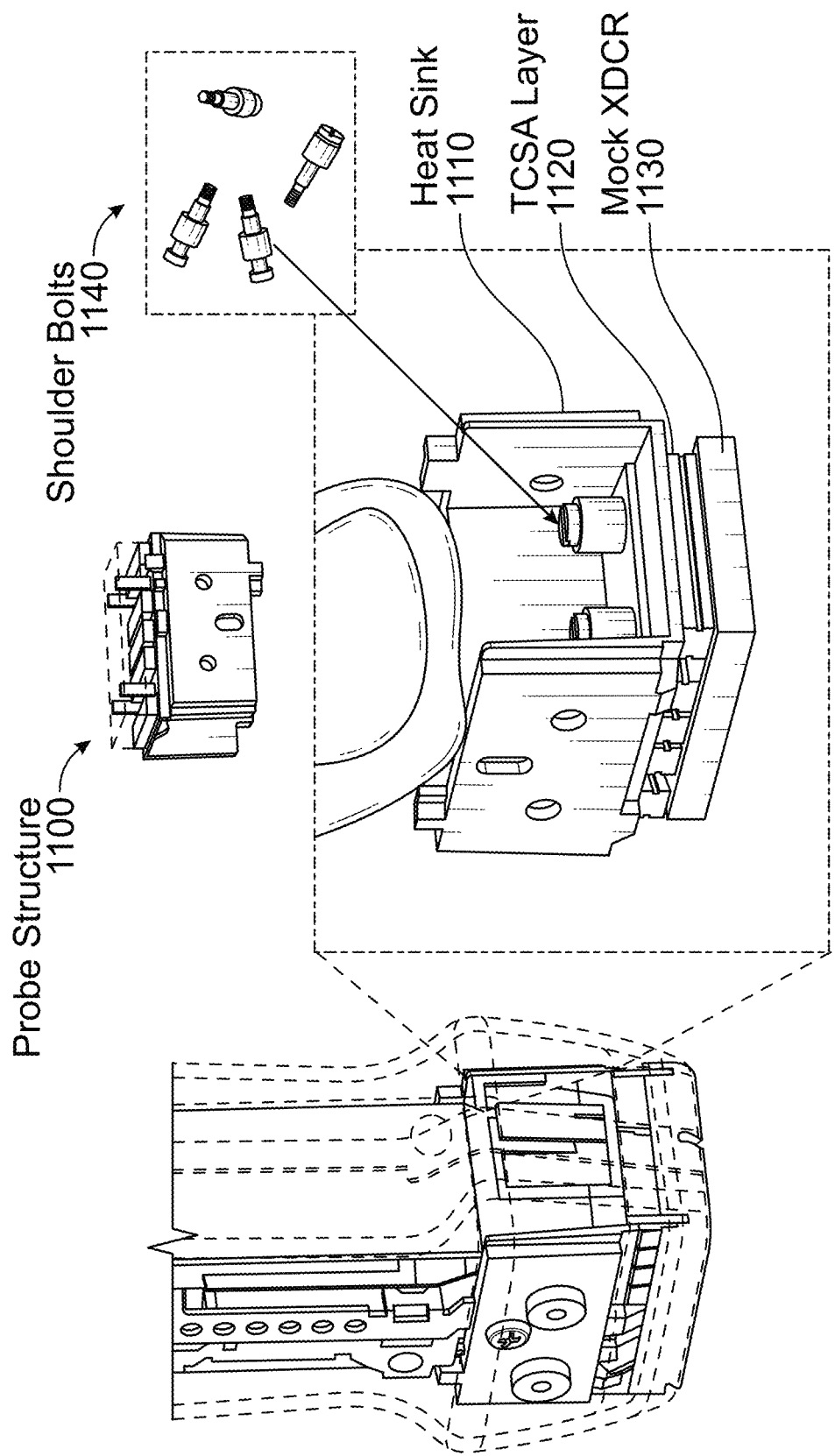
FIG. 11 is a block diagram illustrating a demonstration prototype of medical imaging probe structure with a thermally conductive shock absorber (TCSA) layer.

FIG. 11 is a block diagram illustrating a demonstration prototype of medical imaging probe structure with a thermally conductive shock absorber (TCSA) layer. Shown in FIG. 11 is a probe structure prototype 1100 which may be used as demonstration prototype for illustrating use of thermally conductive shock absorber (TCSA) in accordance with present disclosure.

As shown in FIG. 11, the probe structure prototype 1100 comprises a heat sink 1100, a thermally conductive shock absorber (TCSA) layer 1120, and a mock transducer (xdcr) 1130, with the TCSA layer 1120 comprising 5 TCSA pads. The probe structure prototype 1100 further comprises 4 shoulder bolts (e.g., 0-80 shoulder bolts) 1140 for holding the mock xdcr 1130 (which could also be the stability plate) at a certain spacing from the heat sink 1100, depending on how much each shoulder bolt is screwed into the mock xdcr 1130. The shoulder bolts 1140 also keep the TCSA pads in a state of compression.

As illustrated in FIG. 11, as pressure is applied to the probe structure prototype 1100 and it is rocked around in a circle, the different TCSA pads would correspondingly compress, thus representing the shock absorbing function. As shown in FIG. 11, there may be a small cylindrical spacer between the head(s) of the shoulder bolt(s) 1140 and the heat sink 1100. One way to tune the overall spring constant (stiffness) of the assembly would be to replace that spacer with a spring. In this regard, if the spacer is preplaced with a spring that is in compression, it may counteract the spring force from the TCSA pads and reduce the overall spring constant.

An example medical imaging probe, in accordance with the present disclosure, may be configured for use in a medical imaging system, with the medical imaging probe comprising, at least, a transducer disposed underneath a contact surface of the medical imaging probe, wherein the transducer is configured to transmit and receive signals based on a medical imaging technique; a support structure disposed underneath the transducer; and a thermally conductive shock absorber (TCSA) layer disposed between the transducer and the support structure, wherein the thermally conductive shock absorber (TCSA) layer is configured to facilitate both of thermal transfer in a direction from the contact surface into the support structure, and absorbing at least a portion of impact force applied to at least the contact surface.

In an example embodiment, the transducer comprises processing circuitry configured for supporting or handling processing of transmitted and received signals.

In an example embodiment, when the medical imaging probe is configured for ultrasound imaging, the transducer comprises at least an acoustic stack.

In an example embodiment, when the medical imaging probe is configured for ultrasound imaging, the transducer comprises an acoustic backing disposed between the acoustic stack and the thermally conductive shock absorber (TCSA) layer.

In an example embodiment, the medical imaging probe further comprises a stability plate disposed on top of the thermally conductive shock absorber (TCSA) layer.

In an example embodiment, the thermally conductive shock absorber (TCSA) layer comprises a single thermally conductive shock absorber (TCSA) pad arranged on top of the support structure.

In an example embodiment, the thermally conductive shock absorber (TCSA) layer comprises a plurality of thermally conductive shock absorber (TCSA) elements arranged on a top surface of the support structure.

In an example embodiment, the plurality of thermally conductive shock absorber (TCSA) elements are arranged in one or more levels on top of the support structure.

In an example embodiment, the plurality of thermally conductive shock absorber (TCSA) elements are arranged in N×M arrangements over a surface of the support structure, and wherein each of N and M is integer that is equal to or greater than 1.

In an example embodiment, the thermally conductive shock absorber (TCSA) layer further comprises one or more spring elements disposed among the plurality of thermally conductive shock absorber (TCSA) elements.

In an example embodiment, the thermally conductive shock absorber (TCSA) layer comprises at least one of each of a flexible thermal sheet and a spring element.

In an example embodiment, the medical imaging probe further comprises one or more thermally conductive shock absorber (TCSA) pads disposed within side sections of the medical imaging probe and surrounding at least the transducer.

In an example embodiment, the thermally conductive shock absorber (TCSA) layer comprises at least one thermally conductive shock absorber (TCSA) element that comprises a plurality of sub-sections, and wherein the plurality of sub-sections comprises at least one thermal sub-section and at least one flexible sub-section.

In an example embodiment, the at least one thermal sub-section comprises synthetic graphite.

In an example embodiment, the at least one thermal sub-section comprises metal foil.

In an example embodiment, the at least one flexible sub-section comprises foam or other flexible material.

In an example embodiment, the plurality of sub-sections comprises an outer cover.

In an example embodiment, the plurality of sub-sections comprises an internal void.

In an example embodiment, the plurality of sub-sections is arranged in concentric manner.

In an example embodiment, the support structure comprises a heat sink.

As utilized herein the terms "circuits" and "circuitry" refer to physical electronic components (e.g., hardware) and any software and/or firmware ("code") which may configure the hardware, be executed by the hardware, and or otherwise be associated with the hardware. As used herein, for example, a particular processor and memory may comprise a first "circuit" when executing a first one or more lines of code and may comprise a second "circuit" when executing a second one or more lines of code. As utilized herein, "and/or" means any one or more of the items in the list joined by "and/or". As an example, "x and/or y" means any element of the three-element set {(x), (y), (x, y)}. In other words, "x and/or y" means "one or both of x and y." As another example, "x, y, and/or z" means any element of the seven-element set {(x), (y), (z), (x, y), (x, z), (y, z), (x, y, z)}. In other words, "x, y and/or z" means "one or more of x, y, and z." As utilized herein, the terms "block" and "module" refer to functions than can be performed by one or more circuits. As utilized herein, the term "exemplary" means serving as a non-limiting example, instance, or illustration. As utilized herein, the terms "for example" and "e.g.," set off lists of one or more non-limiting examples, instances, or illustrations. As utilized herein, circuitry is "operable" to perform a function whenever the circuitry comprises the necessary hardware (and code, if any is necessary) to perform the function, regardless of whether performance of the function is disabled or not enabled (e.g., by some user-configurable setting, a factory trim, etc.).

Other embodiments of the invention may provide a non-transitory computer readable medium and/or storage medium, and/or a non-transitory machine readable medium and/or storage medium, having stored thereon, a machine code and/or a computer program having at least one code section executable by a machine and/or a computer, thereby causing the machine and/or computer to perform the processes as described herein.

Accordingly, the present disclosure may be realized in hardware, software, or a combination of hardware and software. The present invention may be realized in a centralized fashion in at least one computing system, or in a distributed fashion where different elements are spread across several interconnected computing systems. Any kind of computing system or other apparatus adapted for carrying out the methods described herein is suited. A typical combination of hardware and software may be a general-purpose computing system with a program or other code that, when being loaded and executed, controls the computing system such that it carries out the methods described herein. Another typical implementation may comprise an application specific integrated circuit or chip.

Various embodiments in accordance with the present disclosure may also be embedded in a computer program product, which comprises all the features enabling the implementation of the methods described herein, and which when loaded in a computer system is able to carry out these methods. Computer program in the present context means any expression, in any language, code or notation, of a set of instructions intended to cause a system having an information processing capability to perform a particular function either directly or after either or both of the following: a) conversion to another language, code or notation; b) reproduction in a different material form.

While the present invention has been described with reference to certain embodiments, it will be understood by those skilled in the art that various changes may be made and equivalents may be substituted without departing from the scope of the present invention. In addition, many modifications may be made to adapt a particular situation or material to the teachings of the present invention without departing from its scope. Therefore, it is intended that the present invention not be limited to the particular embodiment disclosed, but that the present invention will include all embodiments falling within the scope of the appended claims.

What is claimed is:

1. A medical imaging probe configured for use in a medical imaging system, the medical imaging probe comprising, at least:
   a transducer disposed underneath a contact surface of the medical imaging probe, wherein the transducer is configured to transmit and receive signals based on a medical imaging technique;
   a support structure disposed underneath the transducer, wherein the support structure is rigidly secured within the medical imaging probe via one or more rigid connectors; and
   a thermally conductive shock absorber (TCSA) layer disposed between the transducer and the support structure,
   wherein the thermally conductive shock absorber (TCSA) layer is configured to facilitate both of thermal transfer in a direction from the contact surface into the support structure, and absorbing at least a portion of impact force applied to at least the contact surface, and
   wherein the thermally conductive shock absorber (TCSA) layer comprises:
      a plurality of thermally conductive shock absorber (TCSA) elements, wherein each thermally conductive shock absorber (TCSA) element comprises a flexible core that provides absorbing of at least a portion of the impact force and a thermal cover around the flexible core that provides thermal pathway for at least a portion of the thermal transfer; and
      a plurality of physical elements configured to absorb at least a portion of the impact force, wherein the physical elements are separate and different from the thermally conductive shock absorber (TCSA) elements, and wherein the physical elements are disposed among the thermally conductive shock absorber (TCSA) elements within the thermally conductive shock absorber (TCSA) layer.

2. The medical imaging probe of claim 1, wherein the transducer comprises processing circuitry configured for supporting or handling processing of transmitted and received signals.

3. The medical imaging probe of claim 1, wherein, when the medical imaging probe is configured for ultrasound imaging, the transducer comprises at least an acoustic stack.

4. The medical imaging probe of claim 3, wherein, when the medical imaging probe is configured for ultrasound imaging, the transducer comprises an acoustic backing disposed between the acoustic stack and the thermally conductive shock absorber (TCSA) layer.

5. The medical imaging probe of claim 1, further comprising a stability plate disposed on top of the thermally conductive shock absorber (TCSA) layer.

6. The medical imaging probe of claim 1, wherein the thermally conductive shock absorber (TCSA) layer comprises a single thermally conductive shock absorber (TCSA) pad arranged on top of the support structure.

7. The medical imaging probe of claim 1, wherein the plurality of thermally conductive shock absorber (TCSA) elements are arranged on one or both of a top surface of the support structure or a bottom surface of the transducer.

8. The medical imaging probe of claim 1, wherein the plurality of thermally conductive shock absorber (TCSA) elements are arranged in one or more levels.

9. The medical imaging probe of claim 1, wherein the plurality of thermally conductive shock absorber (TCSA) elements are arranged in N×M arrangements, and wherein each of N and M is an integer that is equal to or greater than 1.

10. The medical imaging probe of claim 1, wherein the thermally conductive shock absorber (TCSA) layer further comprises one or more spring elements disposed among the plurality of thermally conductive absorber (TCSA) elements.

11. The medical imaging probe of claim 1, wherein the thermally conductive shock absorber (TCSA) layer comprises at least one of each of a flexible thermal sheet and a spring element.

12. The medical imaging probe of claim 1, further comprising one or more thermally conductive shock absorber (TCSA) pads disposed within side sections of the medical imaging probe and surrounding at least the transducer.

13. The medical imaging probe of claim 1, wherein the thermally conductive shock absorber (TCSA) layer comprises at least one thermally conductive shock absorber (TCSA) element that comprises a plurality of sub-sections, and wherein the plurality of sub-sections comprises at least one thermal sub-section and at least one flexible sub-section.

14. The medical imaging probe of claim 13, wherein the at least one thermal sub-section comprises synthetic graphite.

15. The medical imaging probe of claim 13, wherein the at least one thermal sub-section comprises metal foil.

16. The medical imaging probe of claim 13, wherein the at least one flexible sub-section comprises foam or other flexible material.

17. The medical imaging probe of claim 13, wherein the plurality of sub-sections comprises an outer cover.

18. The medical imaging probe of claim 13, wherein the plurality of sub-sections comprises an internal void.

19. The medical imaging probe of claim 13, wherein the plurality of sub-sections is arranged in concentric manner.

20. The medical imaging probe of claim 1, wherein the support structure comprises a heat sink.

* * * * *